US009636007B2

(12) United States Patent
Hoberman et al.

(10) Patent No.: US 9,636,007 B2
(45) Date of Patent: May 2, 2017

(54) METHOD AND APPARATUS FOR AIDING IN THE DIAGNOSIS OF OTITIS MEDIA BY CLASSIFYING TYMPANIC MEMBRANE IMAGES

(71) Applicants: UNIVERSITY OF PITTSBURGH—OF THE COMMONWEALTH SYSTEM OF HIGHER EDUCATION, Pittsburgh, PA (US); CARNEGIE MELLON UNIVERSITY, Pittsburgh, PA (US)

(72) Inventors: Alejandro Hoberman, Wexford, PA (US); Jelena Kovacevic, New York, NY (US); Nader Shaikh, Pittsburgh, PA (US); Anupama Kuruvilla, Pittsburgh, PA (US)

(73) Assignees: Carnegie Mellon University, Pittsburgh, PA (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/418,509

(22) PCT Filed: Jun. 11, 2013

(86) PCT No.: PCT/US2013/045123
§ 371 (c)(1),
(2) Date: Jan. 30, 2015

(87) PCT Pub. No.: WO2014/021994
PCT Pub. Date: Feb. 6, 2014

(65) Prior Publication Data
US 2015/0305609 A1    Oct. 29, 2015

Related U.S. Application Data

(60) Provisional application No. 61/679,348, filed on Aug. 3, 2012.

(51) Int. Cl.
*G06F 19/00*    (2011.01)
*A61B 1/227*    (2006.01)
(Continued)

(52) U.S. Cl.
CPC .......... *A61B 1/227* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS 5,847,832 A  * 12/1998 Liskow ................ A61B 5/0064
356/605
2006/0282009 A1    12/2006 Oberg et al.
(Continued)

FOREIGN PATENT DOCUMENTS

KR    10-2009-0128613 A    12/2009
WO    WO2012061697 A1    5/2012

OTHER PUBLICATIONS

International Search Report, Korean Intellectual Property Office, Oct. 22, 2013.

*Primary Examiner* — Siamak Harandi
*Assistant Examiner* — Mai Tran
(74) *Attorney, Agent, or Firm* — Eckert Seamans Cherin & Mellott, LLC; Philip E. Levy

(57) ABSTRACT

A method of aiding the diagnosis of otitis media in a patient includes obtaining image data in a processor apparatus of a computing device, the image data being associated with at least one electronic image of a tympanic membrane of the patient, calculating a plurality of image features, each image feature being calculated based on at least a portion of the image data, classifying the at least one electronic image as
(Continued)

a particular type of otitis media using the plurality of image features, and outputting an indication of the particular type of otitis media. Also, a system for implementing such a method that includes an output device and a computing device.

22 Claims, 8 Drawing Sheets

(51) Int. Cl.
| | |
|---|---|
| *A61B 5/00* | (2006.01) |
| *A61B 5/12* | (2006.01) |
| *G06T 7/00* | (2017.01) |
| *G06T 7/40* | (2017.01) |
| *A61B 1/00* | (2006.01) |
| *A61B 1/04* | (2006.01) |
| *A61B 1/06* | (2006.01) |
| *A61B 5/103* | (2006.01) |

(52) U.S. Cl.
CPC ............... *A61B 1/04* (2013.01); *A61B 1/06* (2013.01); *A61B 5/1032* (2013.01); *A61B 5/12* (2013.01); *A61B 5/7264* (2013.01); *G06F 19/345* (2013.01); *G06T 7/0012* (2013.01); *G06T 7/40* (2013.01); *G06T 7/408* (2013.01); *G06F 19/321* (2013.01); *G06T 2207/10024* (2013.01); *G06T 2207/20076* (2013.01); *G06T 2207/30004* (2013.01)

(56) References Cited

U.S. PATENT DOCUMENTS

| | | |
|---|---|---|
| 2009/0185191 A1 | 7/2009 | Boppart et al. |
| 2011/0290005 A1* | 12/2011 | Hart .................. G01B 11/0658 73/37.9 |
| 2011/0307423 A1* | 12/2011 | Shotton ................ G06K 9/6282 706/12 |
| 2012/0059224 A1 | 3/2012 | Wellen et al. |
| 2012/0147010 A1* | 6/2012 | Schmidt ................ G06F 19/321 345/440 |

\* cited by examiner

 
FIG.4A    FIG.4B
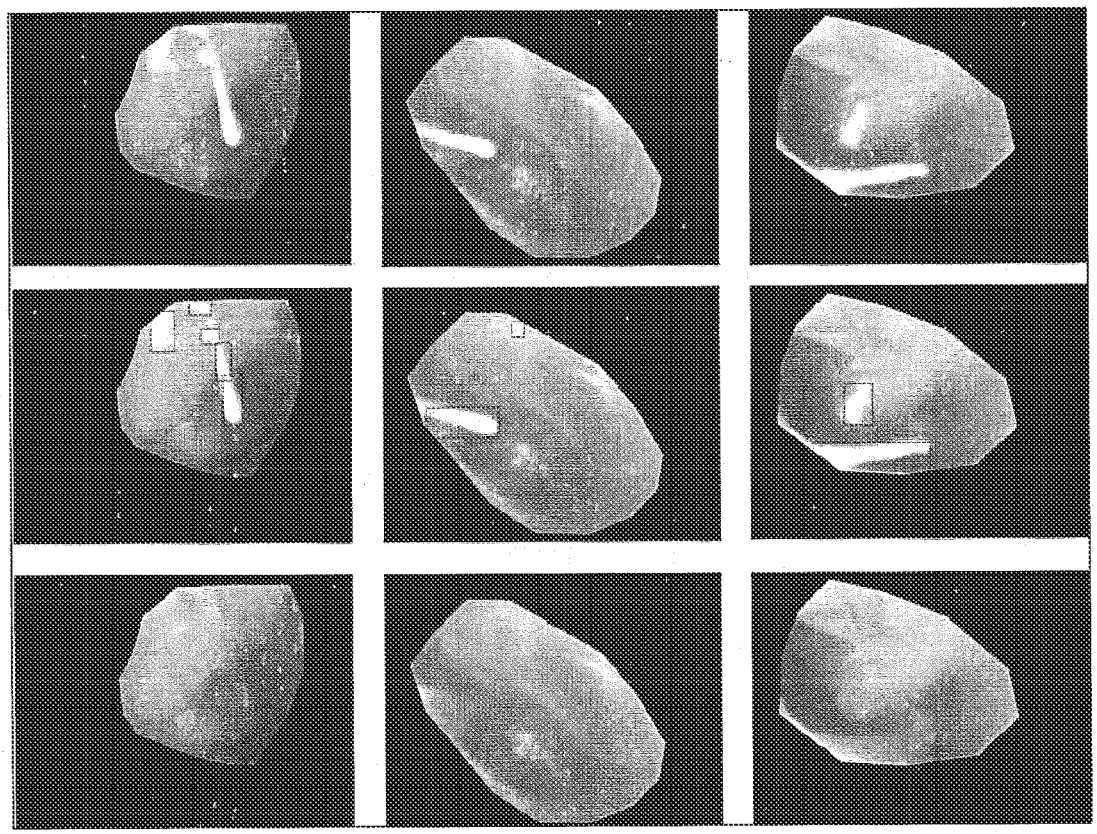
FIG.5

METHOD AND APPARATUS FOR AIDING IN THE DIAGNOSIS OF OTITIS MEDIA BY CLASSIFYING TYMPANIC MEMBRANE IMAGES

CROSS-REFERENCE TO RELATED APPLICATIONS

This application claims priority under 35 U.S.C. §119(e) from U.S. provisional patent application No. 61/679,348, entitled "Otitis Media Vocabulary and Grammar" and filed on Aug. 3, 2012, the contents of which are incorporated herein by reference.

GOVERNMENT CONTRACT

This invention was made with government support under grant #DC010283 awarded by the National Institutes of Health. The government has certain rights in the invention.

BACKGROUND OF THE INVENTION

1. Field of the Invention

The present invention pertains to the diagnosis of otitis media, and in particular, to systems and methods for classifying tympanic membrane images to aid in properly diagnosing otitis media.

2. Description of the Related Art

Otitis media is a general term for middle-ear inflammation and may be classified clinically as either acute otitis media (AOM) or otitis media with effusion (OME). AOM represents a bacterial superinfection of the middle ear fluid. OME, on the other hand, is a sterile effusion that tends to subside spontaneously. Although middle ear effusion is present in both cases, this clinical classification is important because antibiotics are generally beneficial only for AOM. However, proper diagnosis of AOM, as well as distinction from both OME and no effusion (NOE), require considerable training.

AOM is a frequent condition affecting a majority of the pediatric population for which antibiotics are prescribed. It is the most common childhood infection, representing one of the most frequent reasons for visits to the pediatrician. The number of otitis media episodes is substantial, with approximately 11 million visits to office-based physicians in the US and a total of 16 million prescriptions for antimicrobials related to otitis media yearly. This results in significant social burden and indirect costs due to time lost from school and work, with estimated annual medical expenditures for only direct costs of approximately $2 billion.

The current standard of care in diagnosing AOM includes visual examination of the tympanic membrane with a range of available otoscopes: from simple hand-held ones with a halogen light source and low-power magnifying lens, to more sophisticated videootoscopes and otoendoscopes, which connect to a light source (halogen, xenon or LED) and a computer, and can record images and/or video. Single hand-held otoscopes do not permit acquisition of images and/or video and require diagnosis on the spot. In contrast, videootoscopes and otoendoscopes do permit acquisition of images and/or video. In current practice, the clinician views the feed from a videootoscope or otoendoscope on a side screen while holding the device in the ear canal of an often-squirming young child.

The inherent difficulties in distinguishing among the three diagnostic categories of otitis media (AOM, OME, NOE), together with the above issues, make the diagnosis by non-expert otoscopists notoriously unreliable and lead to a number of problems.

One such problem is over-prescription of antibiotics. More specifically, AOM is frequently over-diagnosed. This happens when NOE or OME is misdiagnosed as AOM, typically resulting in unnecessary antibiotic prescriptions that lead to adverse effects and increased bacterial resistance. Over-diagnosis is more common than under-diagnosis because doctors typically try to avoid the possibility of leaving an ill patient without treatment, often leading to antibiotic prescriptions in uncertain cases.

Another such problem is under-prescription of antibiotics. In particular, misdiagnosis of AOM as either NOE or OME leads to under-diagnosis. Most importantly, children's symptoms are left unaddressed. Occasionally, under-diagnosis can lead to an increase in serious complications, such as perforation of the tympanic membrane, and, very rarely, mastoditis.

Still another problem is increased financial costs and burden, as there are direct and indirect financial costs associated with misdiagnosis, such as medication costs, co-payments, emergency department and primary care provider visits, missed work, and special day care arrangements.

For all the reasons above, accurate diagnosis of otitis media is imperative to ensure that antimicrobial therapy is limited to the appropriate patients. This, in turn, increases the likelihood of achieving optimal outcomes and minimizing antibiotic resistance.

SUMMARY OF THE INVENTION

In one embodiment, a method of aiding the diagnosis of otitis media in a patient is provided. The method includes obtaining image data in a processor apparatus of a computing device, the image data being associated with at least one electronic image of a tympanic membrane of the patient, calculating a plurality of image features, each image feature being calculated based on at least a portion of the image data, classifying the at least one electronic image as a particular type of otitis media using the plurality of image features, and outputting an indication of the particular type of otitis media.

The plurality of image features may include: (i) a concavity feature which indicates a degree of concavity of a region located centrally in the tympanic membrane, (ii) a translucency feature which indicates a degree of translucency of the tympanic membrane, (iii) an amber level feature which indicates a degree of amber color present in the tympanic membrane, (iv) a grayscale variance feature which indicates a degree of variance of intensities across a grayscale version of the at least one electronic image, (v) a bubble presence feature which indicates a degree to which bubbles are present in the tympanic membrane, and (vi) a light feature which indicates a degree of non-uniformity of illumination in the at least one electronic image. The plurality of image features may also include a bulging feature which indicates a degree to which the tympanic membrane is bulging, and a malleus presence feature which indicates whether the malleus is visible in the at least one electronic image.

In another embodiment, a system for aiding the diagnosis of otitis media in a patient is provided that includes an output device and a computing device having a processor apparatus structured and configured to obtain image data, the image data being associated with at least one electronic image of a tympanic membrane of the patient, calculate a plurality of image features, each image feature being calculated based on at least a portion of the image data, classify the at least one electronic image as a particular type of otitis media using the plurality of image features, and cause the output device to output an indication of the particular type of otitis media.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 4A and 4B are exemplary computer generated images showing the automated segmentation that may be employed in one exemplary embodiment of the present invention;

FIG. 5 shows a number of exemplary computer generated images and illustrate the specular highlight correction that may be employed in one exemplary embodiment of the present invention;

DETAILED DESCRIPTION OF EXEMPLARY EMBODIMENTS

Figure 1:
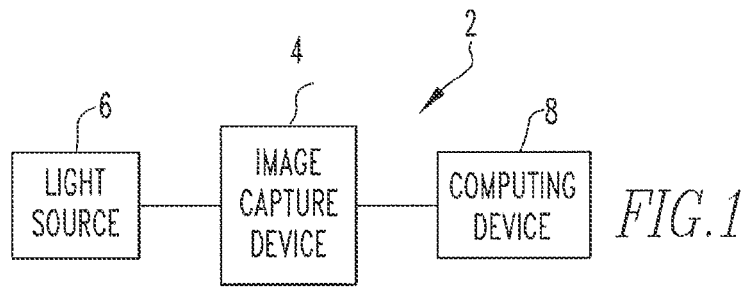
FIG. 1 is a block diagram of a diagnostic system according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention provides, in a number of different embodiments, a method that may serve as a diagnostic aid for otitis media by classifying tympanic membrane images into one of the three stringent clinical diagnostic categories: AOM, OME and NOE. The method comprises a general classification algorithm including at least the following two parts: (i) a numerical feature extraction part meant to discriminate among diagnostic classes, wherein the features are extracted from an image of the tympanic membrane of a patient, and (ii) a classification part based on these extracted features. More specifically, the method employs a feature set (particular embodiments of which are described herein), designed by the inventors, that is understood by both otoscopists and engineers based on the actual visual cues used by otoscopists. This feature set is termed the "otitis media vocabulary". The method further employs a decision process (particular embodiments of which are described herein), designed by the inventors, that combines the vocabulary terms based on the decision processes used by otoscopists. This decision process is termed the "otitis media grammar." In the exemplary implementation, a preprocessing step is employed prior to feature extraction to minimize the impact of image artifacts.

The various particular embodiments of the method, including the feature set (vocabulary) and decision process (grammar), are described in detail herein. First, however, an exemplary diagnostic system 2 in which the method may be implemented (e.g., at least in part as one or more software routines) will be described with reference to FIGS. 1 and 2.

As seen in FIG. 1, diagnostic system 2 includes an image capture device 4 that is structured to be able to capture electronic images from within the auditory canal of a patient, and in particular images of the tympanic membrane of a patient. For example, and without limitation, image capture device 4 may be a videoootoscope or an otoendoscope. A light source 6, such as a halogen source, a xenon source, or an LED, is operatively coupled to image capture device 4 to assist with the image capturing process. Diagnostic system 2 further includes a computing device 8. Computing device 8 is structured to receive electronic image data from image capture device 4 by, for example, a wired or wireless connection. Computing device 8 may be, for example and without limitation, a PC, a laptop computer, a tablet computer, a smartphone, or any other suitable device structured to perform the functionality described herein. Computing device 8 is structured and configured to receive the image data from image capture device 4 and process the data using an embodiment of a method described in detail herein to classify the image data into one of the three stringent clinical diagnostic categories for otitis media, namely AOM, OME and NOE.

Figure 2:
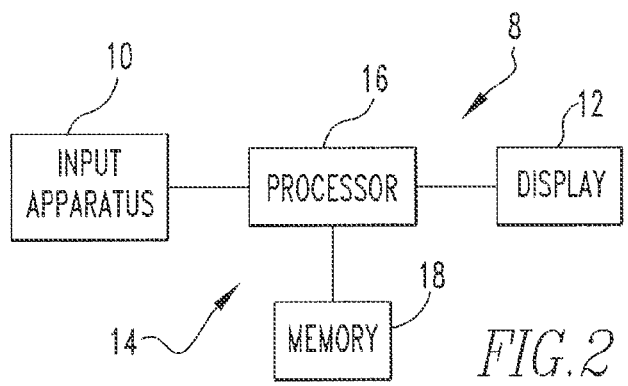
FIG. 2 is a block diagram of one exemplary embodiment of a computing device forming a part of the diagnostic system of FIG. 1.

FIG. 2 is a block diagram of computing device 8 according to one exemplary embodiment. As seen in FIG. 2, the exemplary computing device 8 is a PC and includes an input apparatus 10 (which in the illustrated embodiment is a keyboard), a display 12 (which in the illustrated embodiment is an LCD), and a processor apparatus 14. A user is able to provide input into processor apparatus 14 using input apparatus 10, and processor apparatus 14 provides output signals to display 12 to enable display 12 to display information to the user as described in detail herein. Processor apparatus 14 comprises a processor 16 and a memory 18. Processor 16 may be, for example and without limitation, a microprocessor (μP), a microcontroller, or some other suitable processing device, that interfaces with memory 18. Memory 18 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 18 has stored therein a number of routines that are executable by processor 16. One or more of the routines implement (by way of computer/processor executable instructions) at least one embodiment of the method discussed briefly above and described in greater detail below that is configured to aid in properly diagnosing otitis media by automatically classifying tympanic membrane images.

Figure 3:
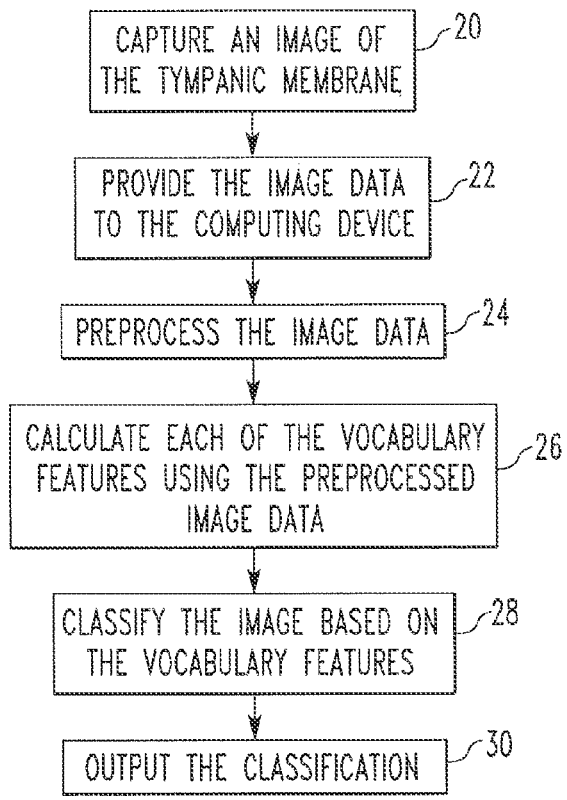
FIG. 3 is a top level flowchart illustrating a method of classifying a tympanic membrane image into an appropriate otitis media diagnostic category according to one exemplary embodiment of the present invention.

FIG. 3 is a top level flowchart illustrating a method of classifying a tympanic membrane image into an appropriate otitis media diagnostic category according to one exemplary embodiment of the present invention. As noted above, at least parts of the method of FIG. 3 may be implemented in one or more routines stored in memory 18 and executable by processor 16 (FIG. 2). Referring to FIG. 3, the method begins at step 20, wherein image capture device 4 is used to capture an image of the tympanic membrane of the patient. Next, at step 22, the image data for the captured image is provided (e.g., in a wired or wireless fashion) to computing device 8. Then, at step 24, processor apparatus 14 preforms certain preprocessing steps on the received image data. The preprocessing performed in step 24 is designed to eliminate or minimize the impact of image artifacts present in and/or associated with the captured image. Such artifacts typically and fundamentally consist of specular highlights. These artifacts will affect the feature computation (described below) and hence ideally should be corrected. In the exemplary embodiment, the preprocessing performed in step 24 employs an automated segmentation process to locate the tympanic membrane, and then applies a local illumination correction process to mitigate the problem of specular highlights. One particular manner in which this type of preprocessing may be performed is described in detail elsewhere herein. If, following the preprocessing, a captured image is deemed not fit for further processing, the method will reject the image and prompt the clinician to retake it (i.e., return to step 20).

Following step 24, the method proceeds to step 26, wherein processor apparatus 14 calculates each of a number of vocabulary features (together referred to as a "feature set") based on and using the preprocessed image data for the captured image. As noted elsewhere herein, each of the vocabulary features in the feature set is designed to in same aspect mimic one or more visual cues used by trained otoscopists when diagnosing otitis media. Two particular, non-limiting feature set embodiments designed by the present inventors, and the methods for calculation thereof, are described in detail elsewhere herein.

Next, at step 28, the vocabulary features in the feature set are used to classify the captured image into one of three clinical diagnostic categories for otitis media, namely: AOM, OME and NOE. In step 28, a decision process (i.e., grammar) which mimics the decision process used by expert otoscopists is used to classify the captured image based on the calculated vocabulary features in the feature set. Two particular, non-limiting decision process embodiments are described in detail elsewhere herein (each one corresponding to a respective one of the particular features set embodiments described herein). Then, at step 30, processor apparatus 14 causes the classification (i.e., the diagnosis of AOM, OME or NOE) to be output to the user by displaying it on display 12.

One particular, non-limiting exemplary embodiment of the preprocessing performed in step 24 will now be described. Segmentation is an important step to extract relevant regions of the captured image on which reliable features for classification can be computed (step 26). In the present embodiment, an active-contour based segmentation algorithm is utilized as follows. First, a so-called snake potential of a grayscale version of the input (captured) image is computed, followed by a set of forces that outline the gradients and edges of the image. The active-contour algorithm is then initialized by a circumference in the center of the image. The algorithm iteratively grows this contour and stops at a predefined convergence criterion, which leaves an outline that covers the relevant region in the image. This outline is used to generate a final mask that is applied to the input (captured) image to obtain the final result. One example of this segmentation, showing an exemplary original image and the resulting segmented image, is provided in FIGS. 4A and 4B.

The present inventors evaluated the performance of the automated segmentation of images as just described against hand segmented images by expert otoscopists, and found that images can be automatically segmented prior to classification without hurting the performance of the overall classifier method. By adding this automated segmentation stage, the classification system becomes completely automated by not requiring the clinician to specify where the tympanic membrane is positioned.

Moreover, one of the problems encountered in processing captured images of the tympanic membrane is the presence of specular highlight regions caused by residual cerumen (wax) in the ear canal, which might remain after the examination. Cerumen often reflects the light from image capture device 4 and light source 6, which typically results in white regions in the image as shown in the top of FIG. 5 (in FIG. 5, AOM is shown in the left, OME is shown in the middle, and NOE is shown on the right). In the present embodiment, these regions of local specular highlights are corrected.

Methods that are robust in correcting local illumination changes include those described in R. Bornard, E. Lecan, L. Laborelli, and J. Chenot, "Missing data correction in still images and image sequences," in *Proc. ACM Int. Conf Multimedia*, Juan-les-Pins, France, 2002, pp. 355-361; M. Varma and A. Zisserman, "Classifying images of materials: Achieving viewpoint and illumination independence," in Proc. Eur. Conf Comput. Vis., May 2002, vol. 3, pp. 255-271; and P. Perez, M. Gangnet, and A. Blake, "Poisson image editing," *ACM Siggraph*, vol. 22, no. 3, pp. 313-318, 2003. Most of these methods adjust the pixel intensity value of the image using a nonlinear mapping function for illumination correction based on the estimated local illumination at each pixel location and combining the adjusted illumination image with the reflectance image to generate an output image. The extent of possible image correction and editing ranges from replacement or mixing with another source image region, to altering some aspects of the original image locally such as illumination or color. Since these methods can be used to locally modify image characteristics, the present embodiment detects the specular highlights in the image and uses one or more of these techniques to locally correct them. In the present embodiment, a simple thresholding scheme on image intensities is used to identify the specular highlight regions as shown in the middle row of FIG. 5, followed by the Poisson image editing technique (see Perez reference above) to correct the identified regions as shown in the bottom row of FIG. 5.

Some of the segmented images may contain large regions of white pixels due to overexposure. The above-mentioned techniques rely on using the neighboring pixels to approximate intensities in the region to be corrected, and thus, are effective when the region to be corrected is small. The present inventors have empirically found that if the area of continuous white pixels is more than 15% of total pixels in the segmented tympanic membrane image, correcting such regions gives unreliable results and hence such an image should be rejected. In the present embodiment, if an image has area of continuous white pixels that is more than 15% of total pixels, it will be rejected and the clinician will be prompted to retake the image (i.e., return to step 20 in FIG. 3) until an image deemed suitable for further processing is obtained.

A particular feature set (vocabulary) and associated decision process (grammar) that may be used in steps 26 and 28 of FIG. 3 according to one particular, exemplary embodiment will now be described in detail. In this embodiment, the feature set includes the following six features, which are each described in more detail below:

$$\begin{cases} \text{concavity } f_c & \text{translucency } f_t & \text{amber level } f_a \\ \text{grayscale variance } f_v & \text{bubble presence } f_b & \text{light } f_l \end{cases}.$$

Figure 6A:
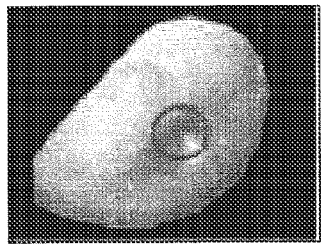
FIGS. 6A-6C are exemplary computer generated images demonstrating the calculation of the central concavity feature of one exemplary embodiment of the present invention.
Figure 6B:
Figure 6C:
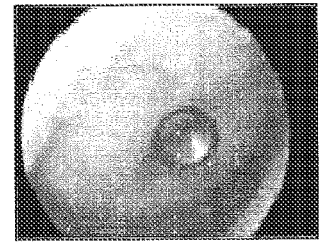

Concavity ($f_c$). The tympanic membrane is attached firmly to the malleus, which is one of the three middle ear bones called auditory ossicles. In the presence of an infection, the tympanic membrane begins to bulge in the periphery. The central region, however, remains attached to the malleus, thereby forming a concavity. In the present embodiment, a feature was designed to identify the concave region located centrally in the tympanic membrane. The feature is called the concavity feature ($f_c$) (or central concavity feature). In calculating this feature, the input is a grayscale version (an example of which is shown in FIG. 6A) of the segmented original RGB image $X \in \mathbb{R}^{M \times N}$ as in FIG. 4B. A sliding window is used to extract a local circular neighborhood, $X_R(m, n)$, of radius R (R=60 in the experiments that were performed by the present inventors). That circular neighborhood is then transformed into its polar coordinates to obtain $X_R(r, \theta)$, with $r \in \{1, 2, \ldots, R\}$, $\theta \in [0, 2\pi]$, and $$r = \sqrt{(m - m_c)^2 + (n - n_c)^2},$$

$$\theta = \arctan\frac{(n - n_c)}{(m - m_c)},$$

where ($m_c$, $n_c$) are the center coordinates of the neighborhood $X_R$. In FIG. 6B, the resulting image has r as the horizontal axis and $\theta$ as the vertical axis. The concave region changes from dark to bright from the center towards the periphery of the concavity; in polar coordinates this change from dark to bright occurs as the radius grows, see FIG. 6B. Defining the bright region B={(r, $\theta$)|r>R'} and the dark region D={(r, $\theta$)|r≤R'}, and with R'$\in$[¼R, ¾R], the ratio of the two means is computed as follows:

$$f_{c,R'} = \frac{E[X_R(r, \theta)|_{(r,\theta) \in B}]}{E[X_R(r, \theta)|_{(r,\theta) \in D}]},$$

As the concave region is always centrally located, a square neighborhood I (here 151×151) is determined to compute the concavity feature as follows:

$$f_c = \max_{R' \in I} f_{c,R'}.$$

Translucency ($f_t$). Translucency of the tympanic membrane is the main characteristic of NOE in contrast with opacity in AOM and semi-opacity in OME; it results in the clear visibility of the tympanic membrane, which is primarily gray. The translucency feature ($f_t$) was designed to measure the grayness of the tympanic membrane. This is done using a simple color-assignment technique based on a number of sample images. As these sample images were taken under different lighting and viewing conditions, at least 3-6 images are needed to characterize a structure/region under all lighting and viewing conditions. The number of images is taken to be $N_{tl}$=20. Then, the following is performed once to determine gray-level clusters in translucent regions: $N_t$ pixels are extracted from translucent regions ($N_t$=100) of $N_{tl}$ RGB images by hand segmentation, to obtain a total of $N_{tl}N_t$ pixels from images (here 2000). These $N_{tl}N_t$ pixels are then clustered using k-means clustering to obtain K cluster centers $c_k \in \mathbb{R}^3$, k=1, 2, . . . , K, capturing variations of gray in the translucent regions. To compute the translucency feature for a given image X, for each pixel (m, n), K Euclidean distances of X(m, n) to the cluster center $c_k$, k=1, 2, . . . , K are computed as follows:

$$d_k(m, n) = \sqrt{\sum_{i=1}^{3} (X_i(m, n) - c_{k,i})^2},$$

with i=1, 2, 3 denoting the color channel. If any of the computed K distances falls below a threshold $T_t$=10 (found experimentally), the pixel is labeled as translucent and belongs to the region $R_t$={(m, n)|$\min_k d_k(m, n) < T_t$}. The binary image $X_t$ is then simply the characteristic function of the region $R_t$, $X_t = \chi_{R_t}$. The translucency feature then defined as the mean of $X_t$ as follows:

$$f_t = E[X_t].$$

Amber level ($f_a$). The fact that OME is predominantly amber or pale yellow may be used to distinguish it from AOM and NOE. Thus, a feature, called the amber level feature ($f_a$), was designed to measure the presence of the color amber in the tympanic membrane. To calculate the amber level feature, a color-assignment technique similar to that used for computing $X_t$ is applied to the captured image to obtain a binary image $X_a$, indicating amber and non-amber regions. The amber level feature is then defined as the mean of $X_a$ as follows:

$$f_a = E[X_a].$$

Grayscale variance ($f_v$). Another discriminating feature among the types of otitis media is the variance of the intensities across the grayscale version of the image $X_v$. For example, OME has a more uniform appearance than AOM and NOE, and consequently has a much lower variance that can be used to distinguish it from AOM and NOE. Thus, a feature, called the grayscale variance ($f_v$), was designed as the variance of the pixel intensities in the image $X_v$ as follows:

$$f_v = \mathrm{var}(X_v).$$

Bubble presence ($f_b$). The presence of visible air-fluid levels, or bubbles, behind the tympanic membrane is an indication of OME. Thus, a feature, called the bubble presence feature ($f_b$), was designed to detect the presence of bubbles in the tympanic membrane. To calculate the bubble presence feature ($f_b$), red and green channels of the original RGB image are input/obtained and Canny edge detection (as described in J. Canny, "A computational approach for edge detection," *IEEE Trans. Pattern Anal. Mach. Intell.*, vol. 8, no. 6, pp. 1293-1299, 1986) is performed thereon to place parallel boundaries on either sides of the real edge, creating a binary image $X_b$ in between. This is followed by filtering and morphological operations to enhance edge detection and obtain smooth boundaries. The bubble presence feature ($f_b$) is then defined as the mean of $X_b$ as follows:

$$f_b = E[X_b].$$

Figure 7A:
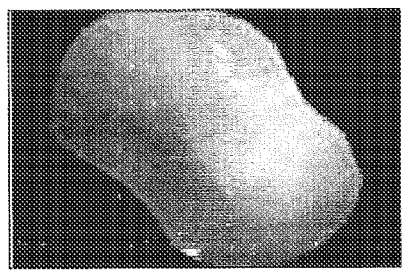
FIGS. 7A-7C are exemplary computer generated images demonstrating the calculation of the light feature of one exemplary embodiment of the present invention.
Figure 7B:
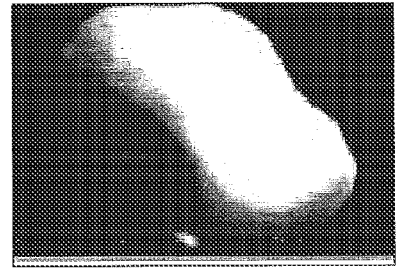
Figure 7C:
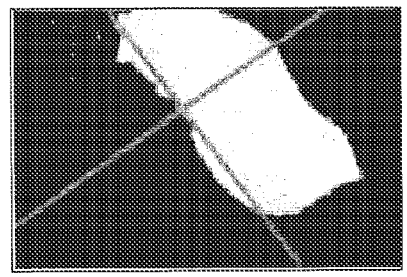

Light $f_{(l)}$. The distinct bulging in AOM results in non-uniform illumination of the tympanic membrane. This is in contrast to the uniform illumination in NOE. Thus, a feature, called the light feature ($f_l$), was designed to measure the non-uniformity of illumination of the captured image as the ratio of the brightly-lit to the darkly-lit regions. To calculate the light feature ($f_l$), a contrast enhancement is performed on the grayscale image version of the captured image as shown in FIG. 7A to make the non-uniform lighting prominent. The resulting image, shown in FIG. 7B, is thresholded at $T_l$ (found experimentally) to obtain a mask of the brightly-lit binary image $X_{bl}$ shown in FIG. 7C. Next, to find the direction ($\theta_{max}$) perpendicular to the maximum illumination gradient, lines passing through ($m_c$, $n_c$) (the pixel coordinates at which $f_c$ is obtained) at the angle $\theta$ with the horizontal axis are examined. Defining the bright region $B = \{(m, n) | n \geq \tan(\theta)(m - m_c) + n_c\}$ and the dark region $D = \{(m, n) | n < \tan(\theta)(m - m_c) + n_c\}$, the ratio of the two means is computed as follows:

$$r(\theta) = \frac{E[X_{b1}(m, n)|_{(m,n) \in B}]}{E[X_{b1}(m, n)|_{(m,n) \in D}]}.$$

Then, the direction perpendicular to the maximum illumination gradient is given by $$\theta_{max} = \arg\max_\theta r(\theta),$$

and the light feature ($f_l$) is defined as:

$$f_l = r(\theta_{max}).$$

The decision process of the present exemplary embodiment for using these six features as just described to classify the captured image as one of AOM, OME and NOE will now be described. The decision process has a hierarchical tree scheme wherein the feature set (vocabulary) is used to discriminate AOM/OME/NOE in the manner described below. In the present embodiment, the hierarchy consists of two levels shown in FIG. 8.

Figure 8:
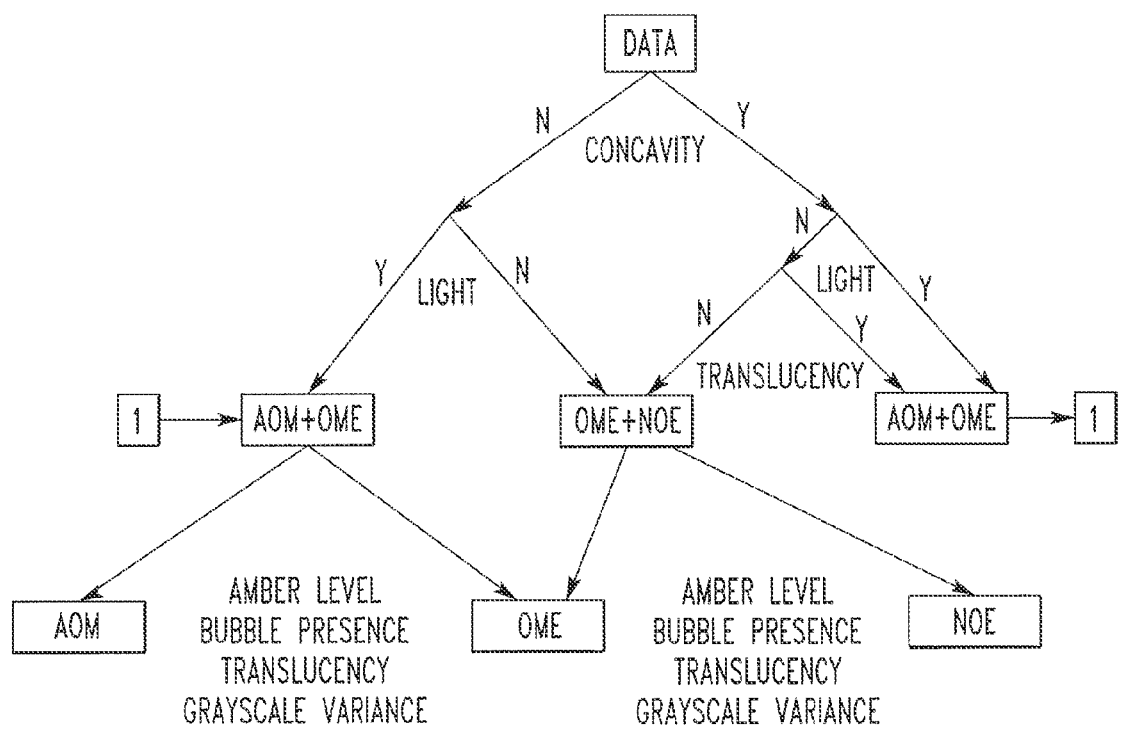
FIG. 8 is a schematic tree diagram showing a decision process for classifying images to diagnose otitis media using a certain feature set according to one embodiment of the invention.

As seen in FIG. 8, at the first level, a coarse separation is performed based on the concavity feature ($f_c$), translucency feature ($f_t$) and the light feature ($f_l$). While ideally, if there is bulging present, the image should be classified as AOM, the concavity feature alone cannot accomplish the task. The light feature is used as an aid as AOM will be non-uniformly lit unlike OME/NOE, as explained earlier. In the second split of the first level, the translucency feature is used to discriminate NOE from the rest. Unfortunately, some of the OME images will show up in the same category due to semi-translucency observed in mild infection. This process results in a separation into two superclasses: AOM/OME (acute/mild infection) and NOE/OME (no/mild infection).

At the second level, a weighted combination of four features, amber level, bubble presence, translucency and grayscale variance, $w_a f_a + w_b f_b + w_t f_t + w_v f_v$, is used to help separate superclasses into individual classes. During a training phase, the weights w that maximize the classification accuracy of training data are determined; these are then used in the testing phase to classify.

The feature set (vocabulary) and associated decision process (grammar) that may be used in steps 26 and 28 of FIG. 3 according to another, alternative particular exemplary embodiment will now be described. In this alternative embodiment, the feature set includes the following eight features:

$$\left\{ \begin{array}{llll} \text{bulging } f_b & \text{central concavity } f_c & \text{light } f_l & \text{malleus presence } f_m \\ \text{translucency } f_t & \text{amber level } f_a & \text{bubble presence } f_{bp} & \text{grayscale variance } f_v \end{array} \right\}.$$

As can be seen above, this embodiment includes six of the same features as the previously described embodiment (concavity ($f_c$) (referred to as central concavity in this embodiment), translucency ($f_t$), amber level ($f_a$), grayscale variance ($f_v$), bubble presence (identified as "fbp" here to distinguish it from the bulging feature described below), and light $f_{(l)}$). This embodiment also includes two additional features, the bulging feature ($f_b$) and the malleus presence feature (fm), which are described in detail below.

In this embodiment, the first three vocabulary features, bulging, central concavity, and light, describe the distinct characteristics associated with AOM, and will be used to construct stage 1 of the decision process associated with this embodiment (described below) to identify AOM. The next two vocabulary features, malleus presence and translucency, are indicative of NOE and will be used to construct stage 2 of the decision process to identify NOE. The final three vocabulary features, amber level, bubble presence, and grayscale variance, describe the characteristics of OME and will be used to construct stage 3 of the decision process to identify OME.

Figure 9A:
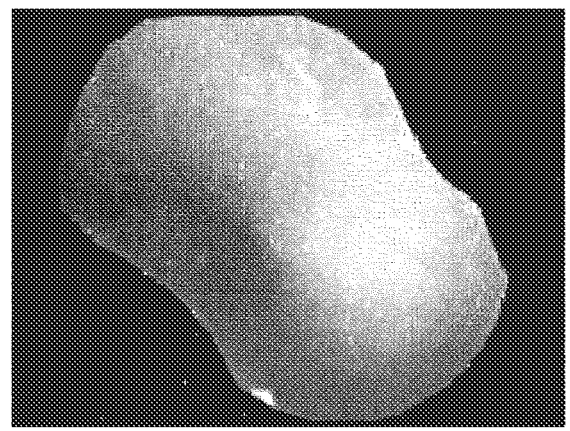
FIGS. 9A and 9B are exemplary computer generated images demonstrating the calculation of the bulging feature of one exemplary embodiment of the present invention.
Figure 9B:
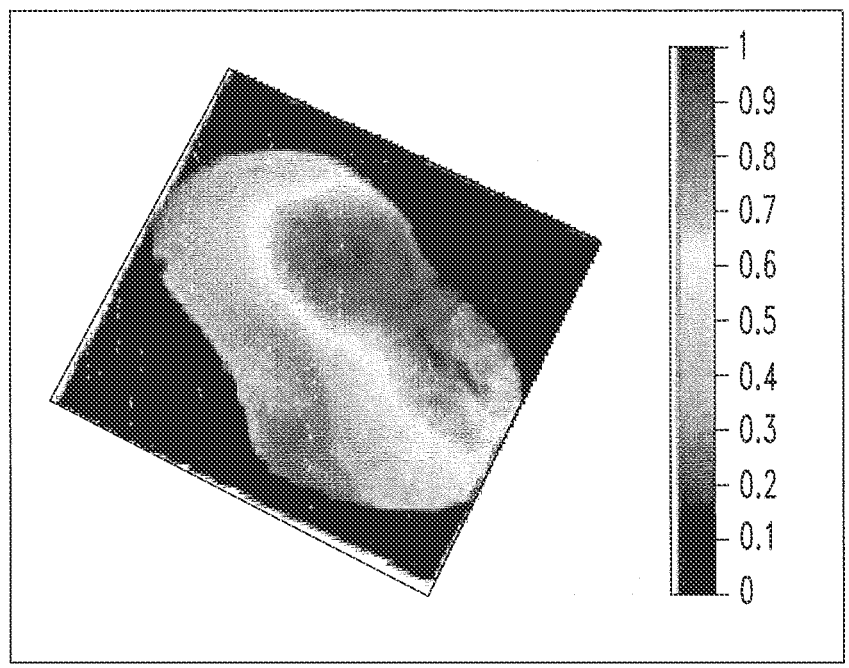

Bulging ($f_b$). The inventors have determined that bulging of the tympanic membrane is very important for properly diagnosing AOM. Thus, a feature, called the bulging feature ($f_b$), was designed that calculates the percentage of the bulged region in the tympanic membrane. The goal is to derive a 3D tympanic membrane shape from a 2D image, by expressing it in terms of depth at each pixel. For example, in AOM, one should be able to identify high-depth variation due to bulging of the tympanic membrane in contrast to low-depth variation in NOE due to tympanic membrane being neutral or retracted. The shape from shading technique described in P. S. Tsai and M. Shah, "Shape from shading using linear approximation," *Image Vis. Comput.*, vol. 12, pp. 487-498, 1994, can be applied to recover a 3D shape from a single monocular image. The input is a grayscale scale version of the segmented original RGB captured image $X \in \mathbb{R}^{M \times N}$ as shown in FIG. 9A. The depth at each pixel can be calculated in an iterative manner using the image gradient and a linear approximation of the reflectance function of the image. FIG. 9B shows the result of depth map $X_d$ identifying the bulged regions in the tympanic membrane. The depth map $X_d$ is then thresholded at $T_d$ (here $T_d$=0.6) to obtain a binary mask $X_b$ of bulging regions in the tympanic membrane. The bulging feature ($f_b$) is then defined as the mean of $X_b$ as follows:

$$f_b = E[X_b].$$

Figure 10A:
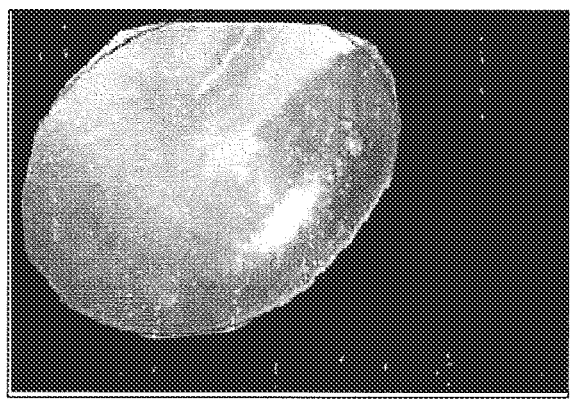
FIGS. 10A-10C are exemplary computer generated images demonstrating the calculation of the malleus presence feature of one exemplary embodiment of the present invention.
Figure 10B:
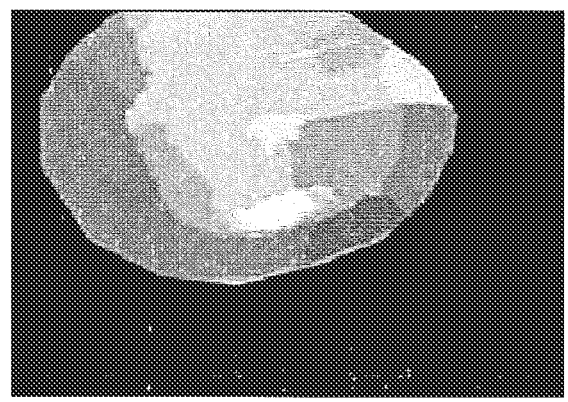
Figure 10C:
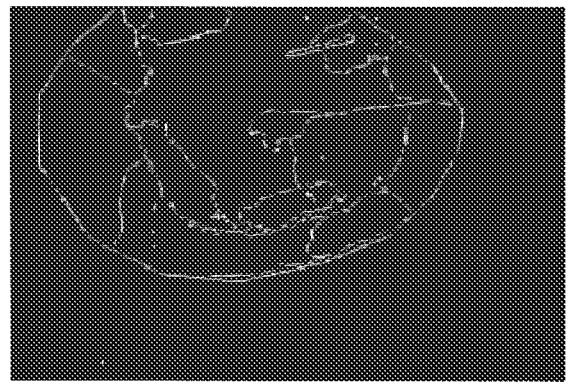

Malleus presence ($f_m$). In OME and in NOE, the tympanic membrane position is either neutral or retracted and makes the short process of the malleus (or hammer bone) visible. Thus, a feature, called malleus presence ($f_m$), was designed to detect the partial or complete appearance of the malleus that would help in distinguishing AOM from OME and NOE. To identify the presence of the malleus, an ellipse fitting process is performed (shown as an outline in FIG. 10A) to identify the major axis. The image is then rotated to align the major axis with the horizontal axis. Mean-shift clustering (as described in Y. Cheng, "Mean shift, mode seeking, and clustering," *IEEE Trans. Pattern Anal. Mach. Intell.*, vol. 17, pp. 790-799, 1995) is then performed as shown in FIG. 10B, followed by Canny edge detection (described elsewhere herein). Hough transform (as described in R. O. Duda and P. E. Hart, "Use of the Hough transform to detect lines and curvesin pictures," *Commun. ACM*, vol. 15, pp. 204-208, January 1977) is applied on the obtained edges around the major axis (50-pixel neighborhood empirically obtained) to detect a straight line (shown at the right in FIG. 10C) extending to the periphery that will indicate the visibility of the malleus. If such a line is detected, then the feature malleus presence $f_m$ is assigned a value of 1 and 0 otherwise.

The decision process of the present exemplary embodiment for using these eight features as just described to classify the captured image as one of AOM, OME and NOE will now be described. The classification is done in three stages by distinguishing one diagnostic category at a time: AOM (Stage 1), NOE (Stage 2), and OME (Stage 3), respectively. Each of these three stags is described in detail below.

Figure 11A:
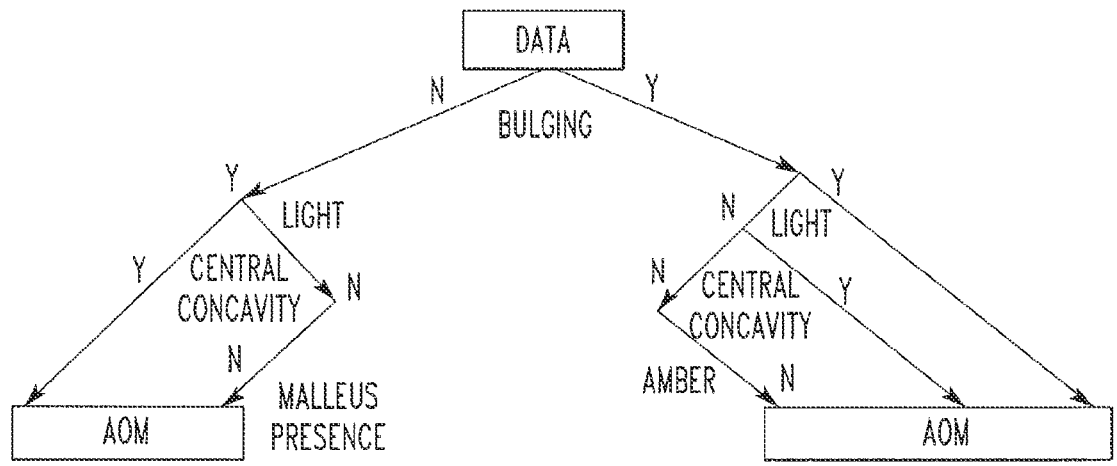
FIGS. 11A-11C are schematic tree diagrams showing a decision process for classifying images to diagnose otitis media using a certain feature set according to an alternative embodiment of the invention.

Stage 1: Identification of AOM. As the first stage, instances of AOM are detected based on the bulging, light, central concavity, and malleus presence features as shown in FIG. 11A. While ideally, if there is bulging present, the image should be classified as AOM, the bulging feature alone cannot accomplish the task. Instead, the other features in the otitis media vocabulary that describe the AOM characteristics such as light, central concavity, and malleus presence are used to aid separation of AOM from NOE and OME. In some cases, OME images can exhibit partial bulging and therefore have a high possibility of being grouped as AOM. In such cases, low amber level is used to distinguish AOM from OME.

Figure 11B:
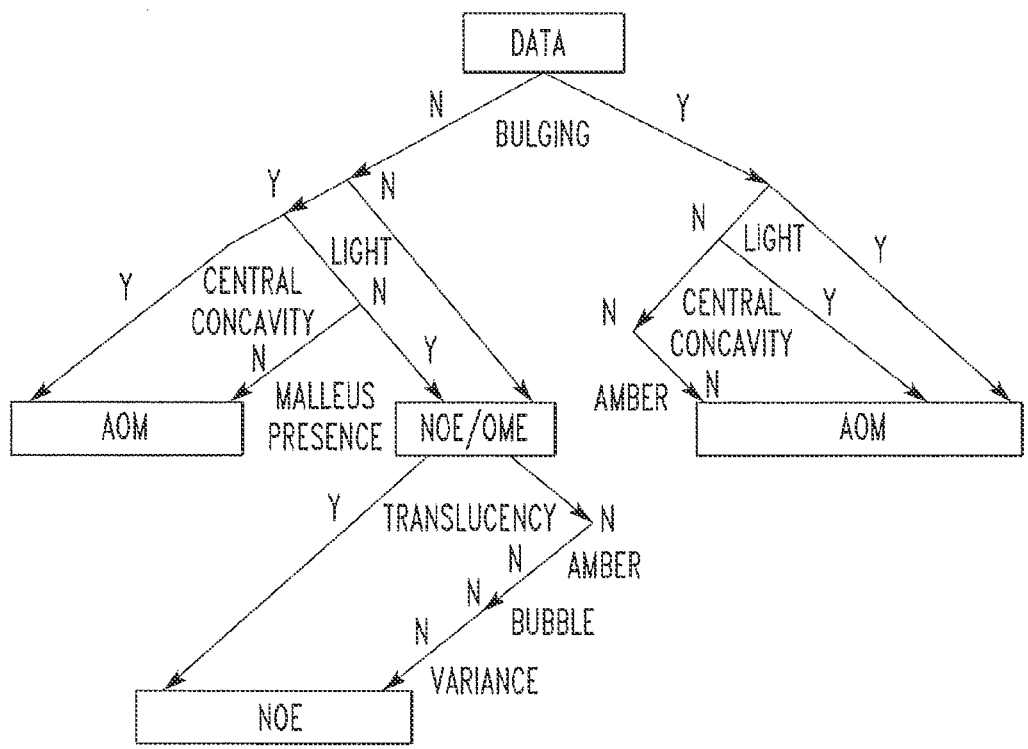

Stage 2: Identification of NOE. Low values of bulging, light, central concavity, and malleus presence features eliminates the possibility of AOM being the diagnosis. Such a situation results in either the diagnosis being NOE or OME, as shown in FIG. 11B (wherein stage 2 has been added to FIG. 11A). In Stage 2, the goal is to distinguish NOE from OME. The translucency feature, which is the most distinguishing characteristic of NOE, can be used here to identify normal cases. A high value of translucency clearly indicates NOE and low values of those features are characteristic of OME indicate NOE. Thus, in this stage, NOE is identified from the super class NOE/OME by a high value of the translucency feature, or low values of all the features characteristic of OME: amber level, bubble presence, and grayscale variance.

Figure 11C:
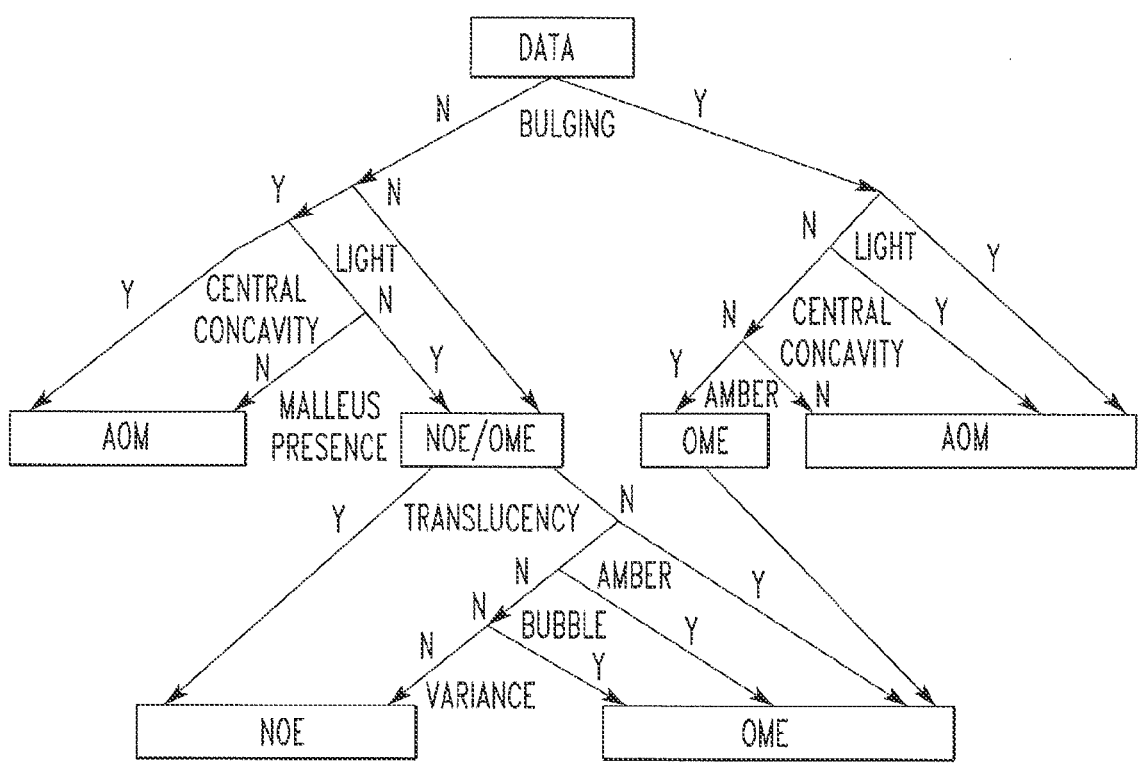

Stage 3: Identification of OME. FIG. 11C shows the complete otitis media grammar of the present embodiment (stage 3 has been added to FIG. 11B. Most of the OME cases are identified from the superclass NOE/OME from Stage 2 as high values of amber level, bubble presence, and grayscale variance features. Some cases of OME can exhibit partial bulging resulting in high values of the bulging feature; in such cases, OME can be correctly detected if the values of light and central concavity features are low, and the value of amber level feature is high.

Thus, the present invention provides, in at least two different particular embodiments, a method that may serve as a diagnostic aid for otitis media by classifying tympanic membrane images into one of the three stringent clinical diagnostic categories: AOM, OME and NOE. Use of the present invention should help to reduce both over-diagnosis and under-diagnosis of otitis media, and, as a result, help ease the financial and social burdens caused thereby.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of aiding a diagnosis of otitis media in a patient, comprising:
   obtaining image data in a processor apparatus of a computing device, the image data being associated with at least one electronic image of a tympanic membrane of the patient;
   calculating a plurality of image features, each image feature being calculated based on at least a portion of the image data, wherein the plurality of image features includes: (i) a concavity feature which indicates a degree of concavity of a region located centrally in the tympanic membrane, (ii) a translucency feature which indicates a degree of translucency of the tympanic membrane, (iii) an amber level feature which indicates a degree of amber color present in the tympanic membrane, (iv) a grayscale variance feature which indicates a degree of variance of intensities across a grayscale version of the at least one electronic image, (v) a bubble presence feature which indicates a degree to which bubbles are present in the tympanic membrane, and (vi) a light feature which indicates a degree of non-uniformity of illumination in the at least one electronic image;
   classifying the at least one electronic image into one of a plurality of predetermined clinical diagnostic categories for otitis media using the plurality of image features and a predetermined decision process; and
   outputting an indication of the one of the plurality of predetermined clinical diagnostic categories.

2. The method according to claim 1, wherein calculating the concavity feature comprises identifying a central region in a grayscale version of the at least one electronic image, defining a bright region in the central region and a dark region in the central region and comparing the bright region to the dark region.

3. The method according to claim 1, wherein calculating the translucency feature comprises measuring a grayness of the tympanic membrane using a color-assignment technique.

4. The method according to claim 1, wherein calculating the amber level feature comprises employing a color-assignment technique.

5. The method according to claim 1, wherein calculating the grayscale variance feature comprises measuring a variance of pixel intensities in the grayscale version of the at least one electronic image.

6. The method according to claim 1, wherein calculating the bubble presence feature comprises obtaining red and green channels of the at least one electronic image, performing edge detection thereon to create a binary image $X_b$ in between edges, and defining as the bubble presence feature the mean of $X_b$.

7. The method according to claim 1, wherein calculating the light feature comprises calculating a ratio of brightly-lit to the darkly-lit regions of the at least one electronic image.

8. The method according to claim 1, wherein the obtaining image data comprises receiving unprocessed image data and preprocessing the unprocessed image data to produce the image data.

9. The method according to claim 8, wherein the preprocessing employs an automated segmentation process to locate the tympanic membrane in the at least one electronic image.

10. The method according to claim 1, wherein the classifying includes a first level based on the concavity feature, translucency feature and the light feature to classify the at least one electronic image into one of two superclasses: AOM/OME and NOE/OME, and a second level to classify the at least one electronic image into one of AOM, OME and NOE based on a weighted combination of the amber level feature, bubble presence feature, the translucency feature and grayscale variance feature.

11. The method according to claim 1, further comprising capturing the at least one electronic image.

12. A system for aiding a diagnosis of otitis media in a patient, comprising:
   an output device; and
   a computing device having a processor apparatus structured and configured to
      obtain image data, the image data being associated with at least one electronic image of a tympanic membrane of the patient;
      calculate a plurality of image features, each image feature being calculated based on at least a portion of the image data, wherein the plurality of image features includes: (i) a concavity feature which indicates a degree of concavity of a region located centrally in the tympanic membrane, (ii) a translucency feature which indicates a degree of translucency of the tympanic membrane, (iii) an amber level feature which indicates a degree of amber color present in the tympanic membrane, (iv) a grayscale variance feature which indicates a degree of variance of intensities across a grayscale version of the at least one electronic image, (v) a bubble presence feature which indicates a degree to which bubbles are present in the tympanic membrane, and (vi) a light feature which indicates a degree of non-uniformity of illumination in the at least one electronic image;
      classify the at least one electronic image into one of a plurality of predetermined clinical diagnostic categories for otitis media using the plurality of image features and a predetermined decision process; and
      cause the output device to output an indication of the one of the plurality of predetermined clinical diagnostic categories.

13. The system according to claim 12, wherein the output device is a display.

14. The system according to claim 12, further comprising an image capture device structured to capture the at least one electronic image.

15. The system according to claim 12, wherein the computing device is structured and configured to calculate the concavity feature by identifying a central region in a grayscale version of the at least one electronic image, defining a bright region in the central region and a dark region in the central region and comparing the bright region to the dark region.

16. The system according to claim 12, wherein the computing device is structured and configured to calculate the translucency feature by measuring a grayness of the tympanic membrane using a color-assignment technique.

17. The system according to claim 12, wherein the computing device is structured and configured to calculate the amber level feature by employing a color-assignment technique.

18. The system according to claim 12, wherein the computing device is structured and configured to calculate the grayscale variance feature by measuring a variance of pixel intensities in the grayscale version of the at least one electronic image.

19. The system according to claim 12, wherein the computing device is structured and configured to calculate the bubble presence feature by obtaining red and green channels of the at least one electronic image, performing edge detection thereon to create a binary image $X_b$ in between edges, and defining as the bubble presence feature the mean of $X_b$.

20. The system according to claim 12, wherein the computing device is structured and configured to calculate the light feature by calculating a ratio of brightly-lit to the darkly-lit regions of the at least one electronic image.

21. The system according to claim 12, wherein the computing device is structured and configured to classify the at least one electronic image using a first level based on the concavity feature, translucency feature and the light feature to classify the at least one electronic image into one of two superclasses: AOM/OME and NOE/OME, and a second level based on a weighted combination of the amber level feature, bubble presence feature, the translucency feature and grayscale variance feature to classify the at least one electronic image into one of AOM, OME and NOE.

22. A computer program product, comprising a non-transitory computer usable medium having a computer readable program code embodied therein, the computer readable program code being adapted to be executed to implement a method for aiding a diagnosis of otitis media in a patient as recited in claim 1.

* * * * *